(12) United States Patent
Xia et al.

(10) Patent No.: US 12,597,131 B2
(45) Date of Patent: Apr. 7, 2026

(54) CHILDREN VISUAL ATTENTION ABNORMAL SCREENING METHOD, INVOLVES EXTRACTING EYE MOVEMENT, FACIAL EXPRESSION AND HEAD MOVEMENT MULTI-MODE CHARACTERISTIC OF CHILDREN BASED ON MULTIMODAL DATA LEARNING

(71) Applicant: NORTHWESTERN POLYTECHNICAL UNIVERSITY, Xi'an City (CN)

(72) Inventors: Chen Xia, Xi'an City (CN); Hexu Chen, Xi'an City (CN); Junwei Han, Xi'an City (CN); Lei Guo, Xi'an City (CN); Kuan Li, Xi'an City (CN); Chi Zhang, Xi'an City (CN); Zhihong Xu, Xi'an City (CN)

(73) Assignee: NORTHWESTERN POLYTECHNICAL UNIVERSITY, Xi'an City (CN)

( * ) Notice: Subject to any disclaimer, the term of this patent is extended or adjusted under 35 U.S.C. 154(b) by 228 days.

(21) Appl. No.: 18/220,743

(22) Filed: Jul. 11, 2023

(65) Prior Publication Data

US 2024/0112330 A1 Apr. 4, 2024

(51) Int. Cl.
*G06T 7/00* (2017.01)
*A61B 5/16* (2006.01)
(Continued)

(52) U.S. Cl.
CPC ............ *G06T 7/0012* (2013.01); *A61B 5/163* (2017.08); *A61B 5/168* (2013.01); *G06T 7/74* (2017.01);
(Continued)

(58) Field of Classification Search
None
See application file for complete search history.

(56) References Cited

U.S. PATENT DOCUMENTS

| | | | |
|---|---|---|---|
| 2015/0169938 A1* | 6/2015 | Yao ....................... | G06V 40/176 382/103 |
| 2016/0004904 A1* | 1/2016 | Senechal ................ | G16H 20/30 382/118 |
| 2019/0251336 A1* | 8/2019 | Wu .......................... | G06F 18/22 |

OTHER PUBLICATIONS

Jones, W., Klin, A. Attention to eyes is present but in decline in 2—6-month-old infants later diagnosed with autism. Nature 504, 427-431 (2013). https://doi.org/10.1038/nature12715.
(Continued)

*Primary Examiner* — Haris Sabah
(74) *Attorney, Agent, or Firm* — HAYNES AND BOONE, LLP

(57) ABSTRACT

The present invention relates to a method for screening mobile terminal visual attention abnormalities in children based on multimodal data learning. A calibration video and a testing video are set up, and a head-face video of children while watching the calibration video and the testing video on smartphones is recorded, respectively. An eye-tracking estimation model is constructed to predict the fixation point location from the head-face video corresponding to the testing video frame by frame and to extract the eye-tracking features. Facial expression features and head posture features are extracted. A Long Short-Term Memory (LSTM) network is used to fuse different modal features and realize the mapping from multimodal features to category labels. In the testing stage, the head-face video of children to be classified while watching the videos on smartphones is recorded, and the features are extracted and input into the post-training model to determine whether they are abnormal.

8 Claims, 6 Drawing Sheets

(51) Int. Cl.

| | | |
|---|---|---|
| *G06T 7/73* | (2017.01) | |
| *G06T 7/80* | (2017.01) | |
| *G06V 10/26* | (2022.01) | |
| *G06V 10/77* | (2022.01) | |
| *G06V 10/80* | (2022.01) | |
| *G06V 10/82* | (2022.01) | |
| *G06V 20/40* | (2022.01) | |
| *G06V 40/16* | (2022.01) | |
| *G06V 40/18* | (2022.01) | |
| *G06V 40/20* | (2022.01) | |

(52) U.S. Cl.
CPC ................ *G06T 7/80* (2017.01); *G06V 10/26* (2022.01); *G06V 10/7715* (2022.01); *G06V 10/811* (2022.01); *G06V 10/82* (2022.01); *G06V 20/46* (2022.01); *G06V 40/171* (2022.01); *G06V 40/176* (2022.01); *G06V 40/193* (2022.01); *G06V 40/20* (2022.01); *A61B 2503/06* (2013.01); *G06T 2207/10016* (2013.01); *G06T 2207/20081* (2013.01); *G06T 2207/20084* (2013.01); *G06T 2207/30041* (2013.01); *G06T 2207/30201* (2013.01)

(56) References Cited

OTHER PUBLICATIONS

Lev, A., Braw, Y., Elbaum, T., Wagner, M., & Rassovsky, Y. (2022). Eye Tracking During a Continuous Performance Test: Utility for Assessing ADHD Patients. Journal of Attention Disorders, 26(2), 245-255. https://doi.org/10.1177/1087054720972786.

Valliappan, N., Dai, N., Steinberg, E. et al. Accelerating eye movement research via accurate and affordable smartphone eye tracking. Nat Commun 11, 4553 (2020). https://doi.org/10.1038/s41467-020-18360-5.

* cited by examiner

CHILDREN VISUAL ATTENTION ABNORMAL SCREENING METHOD, INVOLVES EXTRACTING EYE MOVEMENT, FACIAL EXPRESSION AND HEAD MOVEMENT MULTI-MODE CHARACTERISTIC OF CHILDREN BASED ON MULTIMODAL DATA LEARNING

PRIORITY

This application priority to Chinese patent application serial No. 202211164739.7 filed Sep. 23, 2022, entitled "Method for Screening Mobile Terminal Visual Attention Abnormalities in Children Based on Multimodal Data Learning,", herein incorporated by reference in its entirety.

TECHNICAL FIELD

The present invention relates to the field of computer vision, specifically, to a method for recognizing visual attention abnormalities in children, i.e., the head-face video of children watching videos on smartphones is captured to estimate the eye-tracking location of each video frame, and then multimodal features such as facial expressions and head postures are extracted to achieve screening of visual perception abnormalities in children.

BACKGROUND TECHNIQUE

Visual attention is an important regulatory mechanism of the human visual system and is the key to the effective processing of complex and massive visual inputs. It enables a rational allocation of limited information processing resources so that only the selected subarea of the visual system is analyzed and processed in detail at the current moment, while responses in the space beyond that area are suppressed. So far, most studies on visual attention have been devoted to modeling the common mechanisms presented by different observers, and studies on the differentiation of visual attention processes are limited.

To address this issue, scholars have recently begun to explore the differences in the visual attention processes of different categories of observers and to use comparative experimental analysis to recognize visual attention abnormalities in certain categories of people in order to provide an objective basis for disease screening and recognition and to promote the development of intelligent treatment models. In their article "Attention to eyes is present but in decline in 2-6-month-old infants later diagnosed with autism," Nature, vol. 504, no. 7480, pp. 427-431, 2013, Jones and Klin collected visual attention data separately for children at high risk of autism and children at low risk of autism while watching interactive videos with natural caregivers, along with statistics on the percentage of time spent gazing at the eyes, mouth, body, and objects. The study showed that at 2-6 months of age, children with autism showed abnormal visual attention patterns that differed from those of children with normal development, mainly in the form of shorter fixation times on social scenes and faces. In their article "Eye tracking during a continuous performance test: Utility for assessing ADHD patients," Journal of Attention Disorders, vol. 26, no.2, pp. 245-255, 2022, Lev et al. compared visual attention data from 35 adults with attention deficit and hyperactivity disorder and control observers under different tasks, and uncovered that individuals with attention deficit and hyperactivity disorder spent significantly more time gazing at irrelevant areas on and off the screen.

It should be noted that previous studies of visual attention abnormalities have focused on eye-tracking analysis, and for eye-tracking, eye-trackers have been used in current work to record primary eye-tracking data such as the distribution patterns of observers' visual attention. However, the cost of eye-trackers is usually high, which has limited the development and promotion of visual attention abnormality screening studies to a certain extent. Therefore, studies on eye-tracking estimation on mobile terminals such as smartphones have emerged in recent years. In their article "Accelerating eye-tracking research via accurate and affordable smartphone eye tracking." Nature Communications, vol. 11, no.1, pp. 1-12, 2020, Valliappa et al. constructed a mobile eye-tracking estimation model based on deep learning and compared it with a traditional head-mounted eye-tracker in several visual attention tasks such as visual search, verifying the feasibility of implementing eye-tracking tracking using smartphone cameras in specific visual attention tasks. On the other hand, for visual attention processes, previous studies have often neglected the data on modalities other than eye-tracking, such as facial expressions and head postures. However, these data can also reflect abnormalities in visual attention processes and play an important role in screening visual attention abnormalities.

SUMMARY

Technical Problems to be Solved

In order to avoid the shortcomings of the prior art, the present invention provides a method for screening mobile visual attention abnormalities in children based on multimodal data learning.

Technical Solutions

A method for screening mobile visual attention abnormalities in children based on multimodal data learning, comprising the following steps:

Step 1: A calibration video and a testing video are set up and the head-face videos of m children with visual attention abnormalities and m children with normal development while watching the calibration video and the testing video on smartphones are recorded, respectively. In the context of the present application, m represents an integer having a value of two or greater;

Step 2: An eye-tracking estimation model is constructed. The eye-tracking estimation model is used to estimate the fixation point location of the head-face video frames corresponding to the testing video. Eye-tracking features from the fixation point jump magnitude, fixation point jump angle, and area of interest are extracted;

Step 3: Facial expression features and head movement features are extracted from the head-face videos corresponding to the testing video and then the different modal features are fused using the Long Short-Term Memory (LSTM) network to achieve the mapping from multimodal features to category labels;

Step 4: In the testing stage, the head-face video of children to be classified while watching the mobile video is recorded, and the multimodal features such as eye-tracking, facial expressions, and head movements are extracted and input into the post-training LSTM network model to determine whether they are abnormal.

A further technical solution of the present invention: Step 1, is specified as follows:

Two calibration videos and one testing video are played using a smartphone application while the head-face videos corresponding to m children with abnormal visual attention and m children with normal development while watching calibration video 1, calibration video 2, and testing video, are recorded respectively;

Calibration video 1: a 72-second video, with a black background, green dots, 40 dots flashing randomly, lit randomly for 1.8 seconds at each location and varying in size by 18-50 pixels;

Calibration video 2: a 72-second video, with a black background, green dots moving along the screen in a zigzag pattern, 1.8 seconds per dot, 40 dots moving smoothly;

Testing video: a 2-minute video, consisting of a short video of a children's puzzle game stitched together with a video of geometric changes;

The smartphone is placed horizontally, the child sits at a distance of about 30 cm-40 cm from the smartphone to watch the smartphone video, and the smartphone camera is used to record the head-face video of the child while the video is played.

In a further technical solution of the present invention: Step 2, an eye-tracking estimation model is constructed as follows:

First, the video frames are sampled from the head-face videos corresponding to the two calibration videos, and the face and left and right eyes in each frame are detected using a Single Shot MultiBox Detector to obtain the face image, the left and right eye images, and the corresponding bounding boxes. Next, the face and left and right eye images are transformed into fixed size, the corresponding bounding boxes are normalized, and the features are extracted from the face and left and right eye images respectively by using the convolutional neural network, wherein the left and right eyes share the convolutional neural network weights. Then, the features of the corresponding bounding boxes are extracted by using the fully connected layer to obtain the relative location features of the face and left and right eyes in the images. Finally, the features extracted from the above-mentioned layers are fused by using the fully connected layer, and the final eye-tracking estimation results are obtained by the fully connected layer.

In a further technical solution of the present invention: Step 3, the facial expression features are extracted as follows: Under each video frame, the face is detected and cropped using LibFaceDetection technology. If no face is detected, the video frame is marked as no face detected, and if a face is detected, the cropped face data is input to a trained facial expression recognition network for classification and recognition. Finally, the facial expression recognition results of all frames in each video are counted to generate the facial expression histogram.

In a further technical solution of the present invention: Step 3, the head movement features include head posture features and head movement distance features, wherein the method for extracting head posture features comprising: a constrained local neural field facial feature detector is used to estimate different head posture angles, and then the head postures are classified and divided by setting a threshold, wherein the head posture angles include: head pitch angle p, head deviation angle y, and head roll angle r. According to the three head posture angles, the specific division of head posture is shown as follows:

$$\begin{cases} p_1(\text{Up}), \ p \le -5° \\ p_2(\text{Still}), \ -5° \le p \le -5° \\ p_3(\text{Down}), \ p \ge 5° \end{cases}$$

$$\begin{cases} y_1(\text{Turn left}), \ y \le -5° \\ y_2(\text{Still}), \ -5° \le y \le -5° \\ y_3(\text{Turn right}), \ y \ge 5° \end{cases}$$

$$\begin{cases} r_1(\text{Skew to left}), \ r \le -5° \\ r_2(\text{Still}), \ -5° \le r \le -5° \\ r_3(\text{Skew to right}), \ r \ge 5° \end{cases}$$

A method for extracting head movement distance features, comprising: Firstly, the 3D coordinates of the middle point of the two eyes are estimated to locate the head, then the Euclidean distance of the head locating point on the stereoscopic space for every two adjacent frames is calculated to measure the head movement distance, and finally the head movement distance is divided quantitatively at five intervals.

In a further technical solution of the present invention: Step 3, an LSTM network is used to establish the mapping relationship between multimodal feature sequences and classification labels, as follows:

For the head-face videos of m children with visual attention abnormalities and m children with normal development, while watching the testing video, the head-face videos are sampled at a fixed frequency, and finally, M frames of data are extracted from the total video of each observer for feature extraction, then the multimodal feature sequence of each observer's video is $F=\{F_1, F_2, \ldots, F_i, \ldots \}$, where $F_i$ refers to the multimodal feature corresponding to the ith segment;

$F_i$ consists of the eye-tracking feature $ET_i$, the facial expression feature $FE_i$, and the head movement feature $HM_i$, i.e., $F_i=\{ET_i, FE_i, HM_i\}$, wherein $ET_i$ is the percentage feature of the 5-dimensional histogram of fixation point jump magnitude, 9-dimensional histogram of fixation point jump angle and 4-dimensional semantic region of fixation point corresponding to the $i^{th}$ video segment; $ET_i$ corresponds to the 8-dimensional histogram of facial expressions, and $HM_i$ corresponds to the 9-dimensional histogram of head postures and the 5-dimensional histogram of head movement distances;

The multimodal feature sequences extracted from multiple consecutive video segments are used as input and the corresponding labels are used as output to train the LSTM network, wherein the labels are marked as 1 for children with visual attention abnormalities and 0 for normal children; the mapping relationship between multimodal feature sequences and labels is obtained to realize the construction of the model for screening visual attention abnormalities.

A computer system, comprising: one or more processors, a computer readable storage medium for storing one or more programs, wherein the one or more programs, when executed by the one or more processors, enable the one or more processors to implement the method described above.

A computer readable storage medium, wherein computer executable instructions are stored, and the instructions, when executed, are used to implement the method described above.

Beneficial Effects

The present invention provides a method for screening mobile terminal visual attention abnormalities in children based on multimodal data learning, which has the following beneficial effects:

(1) The present invention is concerned with the problem of differentiation in visual attention. Unlike the traditional analysis research based on statistical theory, in the present invention, a model for recognizing visual attention abnormalities based on a deep neural network from the perspective of learning, to realize the screening of visual attention abnormalities directly using the mobile terminal visual attention data.

(2) For the eye-tracking data, unlike the traditional studies based on the comparison of underlying eye-tracking features, in the present invention, semantic perceptual differences are introduced into the model by setting the area of interest, and the underlying fixation point features are integrated with the high-level semantic features to describe the eye-tracking attributes. On the other hand, in addition to eye-tracking data, the present invention also focuses on other modal visual attention data such as facial expressions and head postures, and the LSTM network is used to fuse different modal features to analyze more comprehensively and reconstruct the visual attention process of observers, reduce the omission ratio, and improve the abnormality recognition ability of the model.

(3) On the basis of the research of visual attention based on eye-trackers, in the present invention, a low-cost and easy-to-promote model for screening visual attention abnormalities is constructed from the collected mobile data, and responds to abnormal behavior in an objective way, which can help promote the screening of large-scale visual attention abnormality diseases in backward and remote areas. It has important research significance and industrial application value.

The present invention can be extended to many types of recognition and classification applications based on visual attention abnormalities such as autism recognition, attention deficit, and hyperactivity disorder recognition by changing the training samples, and can also be used as features and in combination with other machine learning methods for target detection and recognition applications.

BRIEF DESCRIPTION OF THE DRAWING FIGURES

The drawings are for the purpose of illustrating specific embodiments only and are not to be considered a limitation of the present invention. Throughout the drawings, the same reference symbols indicate the same components.

DETAILED DESCRIPTION

Figure 1:
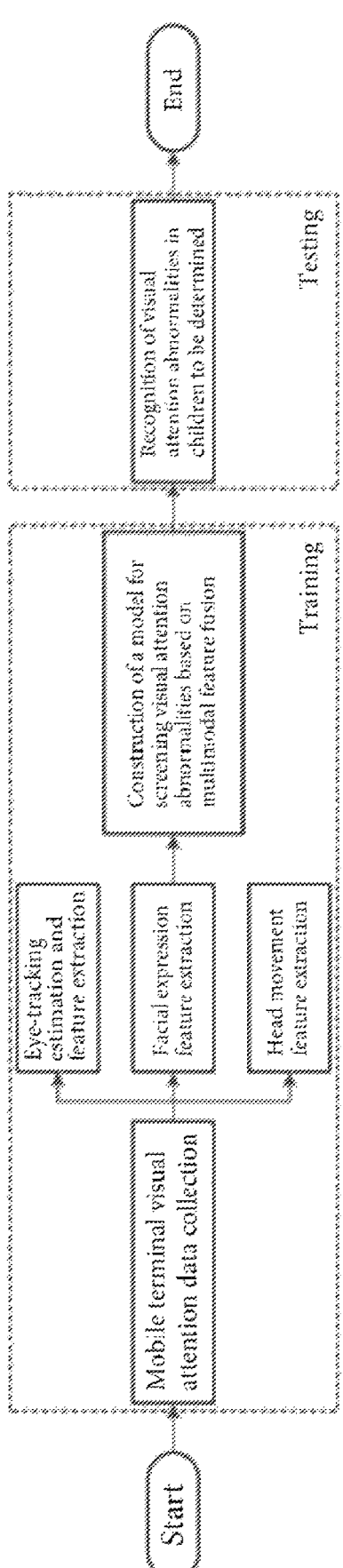
FIG. 1 is a general flow chart of the realization of the present invention.

In order to make the purpose, technical solutions, and advantages of the present invention more clearly understood, the present invention is described in further detail hereinafter in conjunction with the drawings and embodiments. It should be understood that the embodiments described herein are intended to explain the present invention only and are not intended to limit it. In addition, the technical features involved in various embodiments of the present invention described below can be combined with each other as long as they do not constitute a conflict between them.

The technical solution of the present invention is: First, a calibration video and a testing video are set up, and the head-face videos of m children while watching the calibration video and the testing video on smartphones are recorded, respectively. Second, an eye-tracking estimation model is constructed to estimate the fixation point location of the head-face video frames corresponding to the testing video, and eye-tracking features from the fixation point jump magnitude, fixation point jump angle, and the area of interest are extracted. Next, facial expression features and head movement features are extracted from the head-face videos corresponding to the testing video and then the different modal features are fused using the Long Short-Term Memory (LSTM) network to achieve the mapping from multimodal features to category labels. Finally, the head-face video of children to be classified while watching the mobile video is recorded, and the features such as eye-tracking, facial expressions, and head postures are extracted and input into the post-training model to determine whether they are abnormal. The implementation steps include the following:

(1) Mobile Terminal Visual Attention Data Collection

Two calibration videos and one are played using a smartphone application while the head-face videos corresponding to m children with abnormal visual attention and m children with normal development while watching calibration video 1, calibration video 2, and testing video, are recorded respectively.

Calibration video 1: a 72-second video, with a black background, green dots, 40 dots flashing randomly, lit randomly for 1.8 seconds at each location, and varying in size by 18-50 pixels.

Calibration video 2: a 72-second video, with a black background, green dots moving along the screen in a zigzag pattern, 1.8 seconds per dot, 40 dots moving smoothly.

Testing video: a 2-minute video, consisting of a short video of a children's puzzle game stitched together with a video of geometric changes.

The smartphone is placed horizontally, the child sits at a distance of about 30 cm-40 cm from the smartphone to watch the smartphone video, and the smartphone camera is used to record the head-face video of the child while the video is played.

(2) Eye-Tracking Estimation and Feature Extraction

An eye-tracking estimation model is constructed to predict the fixation point location frame by frame. On the other hand, the eye-tracking features corresponding to each head-face video under the testing video are extracted to prepare for the training of a multimodal model for screening visual attention abnormalities.

① Eye-Tracking Estimation

In order to obtain more accurate eye-tracking estimation results, the general eye-tracking estimation model is first trained using the head-face video recorded by the smartphone camera during the playback of calibration video 1 in the data of m children with normal development, and then the general eye-tracking estimation results are individually calibrated using the head-face video recorded during the playback of calibration video 2. In the model training process, the center coordinates of the green origin of the corresponding video frames are used as the true values of eye-tracking estimation.

First, the video frames are sampled from the head-face videos corresponding to the two calibration videos at 30 frames per second, and the face and left and right eyes in each frame are detected using a Single Shot MultiBox Detector (SSD) to obtain the face image, the left and right eye images, and the corresponding bounding boxes. Next, the face and left and right eye images are transformed into fixed size, the corresponding bounding boxes are normalized, and the features are extracted from the face and left and right eye images respectively by using the convolutional neural network, wherein the left and right eyes share the convolutional neural network weights. Then, the features of the corresponding bounding boxes are extracted by using the fully connected layer to obtain the relative location features of the face and left and right eyes in the images. Finally, the features extracted from the above-mentioned layers are fused by using the fully connected layer, and the final eye-tracking estimation results are obtained by the fully connected layer.

In the eye-tracking estimation model training, the general eye-tracking estimation model is first trained using the data of different observers corresponding to calibration video 1. However, since the general eye-tracking estimation model is trained from different observers' data, and different observers have different intrinsic biases—the intrinsic optical axis visual axis bias (i.e., human kappa angle). Therefore, it is necessary to calibrate the general eye-tracking estimation model using the observer-specific data in calibration video 2 as the calibration training set to fit this inherent bias of different observers. This is done by using the fused features extracted from the general eye-tracking estimation model (i.e., the feature output of the penultimate layer of the general eye-tracking model) as input, and then using support vector regression (SVR) to obtain personalized calibration prediction results, and training the personalized SVR model with the data corresponding to the observer-specific calibration video 2, to obtain more accurate prediction results.

②Eye-Tracking Feature Extraction

The above eye-tracking estimation model is used to estimate the fixation point location of the head-face video frames corresponding to the testing video, and then the eye-tracking features are extracted from three perspectives, such as the fixation point jump amplitude, the fixation point jump angle and the number of fixation points in the semantic region. First, in order to extract the fixation point jump amplitude feature, the Euclidean distance between the fixation point of every two adjacent frames in two-dimensional space is calculated and divided at 5 intervals. Second, in order to extract the fixation point jump angle feature, the angle between the jump line and the X-axis is calculated for the fixation point of every two adjacent frames, and then the 360 degrees is divided into 8 intervals uniformly and without jump to generate 9-dimensional histogram features.

Since the fixation point jump amplitude and the fixation point jump angle are the underlying eye-tracking features, in order to detect visual attention abnormalities from the perspective of semantic perception, first, the areas of interest of the video are marked, and three areas, including the face, the body, and other salient targets besides the human body are marked, and then the percentage of the number of fixation points of the face, body, other salient targets and background in each video to the total number of fixation points of the video is counted as semantic eye-tracking features. In summary, under the eye-tracking modality, each video will correspond to an 18-dimensional feature vector, wherein 14 dimensions are the histogram features of the underlying fixation point jump amplitude and fixation point jump angle, and 4 dimensions correspond to the percentage of fixation points in different semantic regions.

(3) Facial Expression Feature Extraction

The visual attention features of each head-face video under the testing video corresponding to the facial expression modality are extracted to prepare for training a multimodal visual attention abnormality screening model.

First, the face is detected using LibFaceDetection technology, and the face in the video is cropped. LibFaceDetection face detection is faster than the traditional MultiBox feedforward convolutional network algorithm and requires less computing power from the device. If no face is detected, the frame is classified as no face detected. If a face is detected, the segmented area is used for subsequent extraction and classification of facial expression features.

Next, a MobileNetV3-Small network based on transfer learning is used to build a facial expression recognition network to achieve facial expression feature extraction from video data. The MobileNetV3-Small is a network model designed for mobile devices and embedded vision, which makes the model more lightweight and improves inference speed and model accuracy. Transfer learning is a machine learning method that allows a model trained for the first task to be used as an initial model for training a second, different task. In the specific training, ImageNet, an image recognition database is first used to train the MobileNetV3Small main network to obtain the initial parameters for network pre-training, and then two fully connected layers are added to the output of the MobileNetV3-Small network in turn, and a Batch Normalization (BN) layer is added before each fully connected layer. The final layer is connected to the Softmax layer to output the probabilities of seven facial expressions. Based on the construction of the complete facial expression recognition network, Extended Cohn-Kanade Dataset (CK+), a classical facial expression dataset is used to fine-tune the model globally to improve the recognition accuracy and obtain the facial expression recognition model based on the MobileNetV3-Small network.

Finally, the facial expression features are extracted and the histogram of facial expression features is constructed. Under each video frame, the face is detected and cropped using LibFaceDetection technology. If no face is detected, the video frame is marked as no face detected, and if a face is detected, the cropped face data is input to the trained facial expression recognition network for classification and recognition (7 categories of facial expressions: no expression, disgust, anger, sadness, fear, happiness, surprise). Finally, the facial expression recognition results of all frames in each video are counted to generate an 8-dimensional histogram of facial expressions (no expression, disgust, anger, sadness, fear, happiness, surprise, and no face detected). In summary, under the facial expression modality, each video corresponds to the features of the 8-dimensional histogram of facial expressions.

(4) Head Movement Feature Extraction

The visual attention features of each head-face video under the testing video corresponding to the head movement modality are extracted to prepare for training a multimodal model for screening visual attention abnormalities.

Head movement is also an important attribute in the visual attention process and can effectively respond to abnormal visual attention behavior. In the present invention, head movement features are described from two perspectives:

head posture and head movement distance. In order to extract the head posture features, a constrained local neural field (CLNF) facial feature detector is first used to estimate different head posture angles, and then the head posture (down and up, turn left and turn right, skew to left and skew to right) is classified by setting thresholds. The head posture angles include head pitch angle p, head deviation angle y, and head roll angle r. According to the three head posture angles, the head postures are classified as follows:

$$\begin{cases} p_1(\text{Up}), p \le -5° \\ p_2(\text{Still}), -5° \le p \le -5° \\ p_3(\text{Down}), p \ge 5° \end{cases}$$

$$\begin{cases} y_1(\text{Turn left}), y \le -5° \\ y_2(\text{Still}), -5° \le y \le -5° \\ y_3(\text{Turn right}), y \ge 5° \end{cases}$$

$$\begin{cases} r_1(\text{Skew to left}), r \le -5° \\ r_2(\text{Still}), -5° \le r \le -5° \\ r_3(\text{Skew to right}), r \ge 5° \end{cases}$$

In order to extract head movement distance features, firstly, the 3D coordinates of the middle point of the two eyes are estimated to locate the head, then the Euclidean distance of the head locating point on the stereoscopic space for every two adjacent frames is calculated to measure the head movement distance, and finally, the head movement distance is divided quantitatively at five intervals. In summary, under the head movement modality, each video segment corresponds to a 14-dimensional histogram feature, wherein the three head posture angles correspond to a 9-dimensional head posture histogram division and the head movement distance corresponds to 5 histogram interval divisions.

(5) Construction of a Model for Screening Visual Attention Abnormalities Based on Multimodal Feature Fusion Based on the above extraction of multimodal features such as eye-tracking, facial expressions, and head postures from the head-face video segments corresponding to the testing videos, the task of this step is to construct multimodal feature sequences and then establish the mapping relationship between multimodal feature sequences and classification labels using the LSTM network.

First, for the head-face videos of m children with visual attention abnormalities and m children with normal development while watching the testing video, the head-face videos are sampled at a frequency of 10 frames per second, and finally, M frames of data are extracted from the total video of each observer. The 50 frames are used as a segment for feature extraction. The multimodal feature sequence of each observer's video is $F=\{F_1, F_2, \ldots, F_i, \ldots\}$, where $F_i$ refers to the multimodal feature corresponding to the 50 frames of data of the $i^{th}$ segment.

$F_i$ consists of the eye-tracking feature $ET_i$, the facial expression feature $FE_i$, and the head movement feature $HM_i$, i.e., $F_i=\{ET_i, FE_i, HM_i\}$, wherein $ET_i$ is the percentage feature of the 5-dimensional histogram of fixation point jump magnitude, 9-dimensional histogram of fixation point jump angle and 4-dimensional semantic region of the fixation point (face, body, other salient targets, and background) corresponding to the $i^{th}$ video segment. $ET_i$ corresponds to the 8-dimensional histogram of facial expressions, and $HM_i$ corresponds to the 9-dimensional histogram of head postures and the 5-dimensional histogram of head movement distances. In summary, each video segment corresponds to a 40-dimensional multimodal feature vector.

Finally, in order to train the model for screening visual attention abnormalities, the multimodal feature sequences extracted from the total video (multiple consecutive video segments) are used as input, and the corresponding labels (1 for children with visual attention abnormalities and 0 for normal children) are used as an output to train the LSTM network and obtain the mapping relationship between the multimodal feature sequences and the labels to realize the construction of the model for screening visual attention abnormalities.

(6) Recognition of Visual Attention Abnormalities in Children to be Determined

For the children in the category to be determined, the head-face videos are first recorded while watching calibration video 2 and the testing video on smartphones, and the head-face videos corresponding to calibration video 2 are used to fine-tune the eye-tracking estimation network individually.

The head-face video corresponding to the testing video is sampled at a frequency of 10 frames per second, and then the video is segmented into a sequence of 50 frames. For each segment, the 40-dimensional features corresponding to the segment are generated by extracting the eye-tracking, facial expression, and head movement features corresponding to the segment, and then the features of the whole video corresponding to multiple segments are used to build a multimodal feature sequence, which is finally input to the LSTM network for abnormality recognition.

To enable a person skilled in the art to better understand the present invention, the following detailed description of the present invention is provided in conjunction with embodiments.

Embodiment 1: a Method for Screening Autism in Children Based on Multimodal Data Learning According to FIG. 1, the specific implementation steps of the present invention are as follows:

Step 1, Mobile Terminal Visual Attention Data Collection 50 children with autism and 50 children with normal development are recruited for the experiment.

Figure 2:
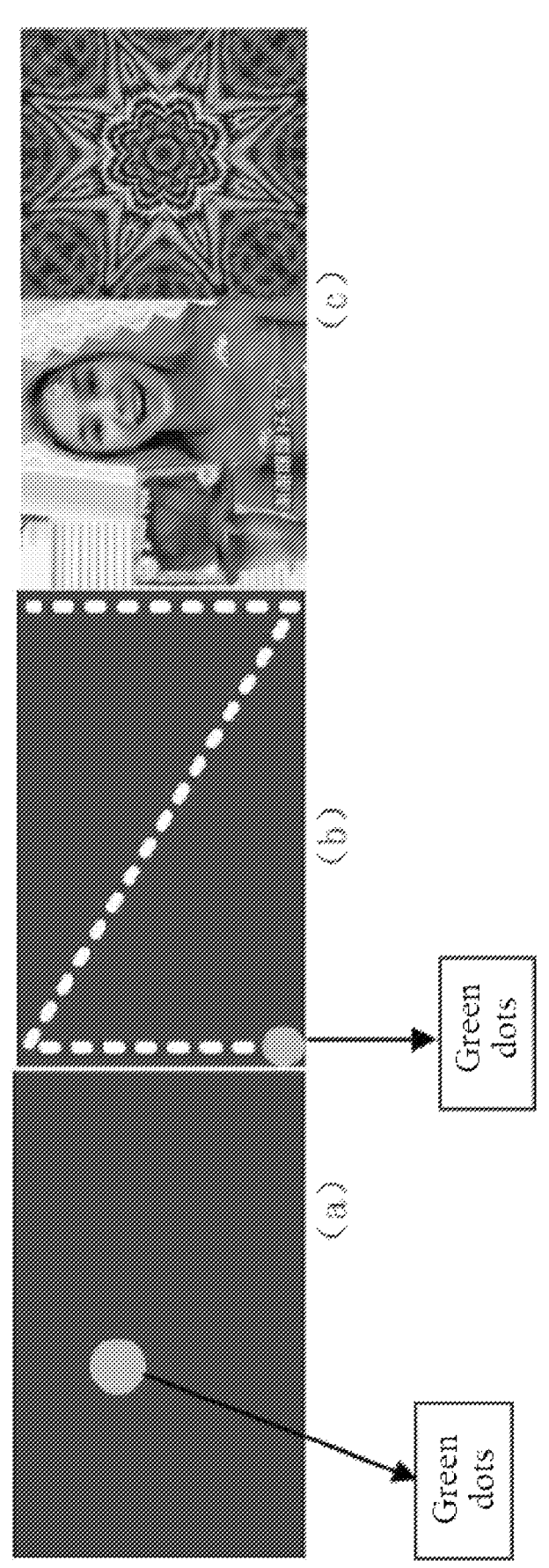
FIG. 2 is a schematic diagram of a mobile calibration video and a testing video in the present invention: (a) schematic diagram of calibration video 1; (b) schematic diagram of calibration video 2; (c) schematic diagram of the testing video.

According to FIG. 2, two calibration videos and one testing video are played using a smartphone application while the head-face videos of children while watching calibration video 1, calibration video 2, and testing video, are recorded respectively.

Calibration video 1: a 72-second video, with a black background, green dots, 40 dots flashing randomly, lit randomly for 1.8 seconds at each location, and varying in size by 18-50 pixels.

Calibration video 2: a 72-second video, with a black background, green dots moving along the screen in a zigzag pattern, 1.8 seconds per dot, 40 dots moving smoothly.

Testing video: a 2-minute video, consisting of a short video of a children's puzzle game stitched together with a video of geometric changes.

The smartphone is placed horizontally, the child sits at a distance of about 30 cm-40 cm from the smartphone to watch the smartphone video, and the smartphone camera is used to record the head-face video of the child while the video is played.

Step 2, Eye-Tracking Estimation and Feature Extraction

An eye-tracking estimation model is constructed to predict the fixation point location frame by frame. On the other hand, the eye-tracking features corresponding to each head-face video under the testing video are extracted to prepare for the training of a multimodal visual attention abnormality screening model.

① Eye-Tracking Estimation

Figure 3:
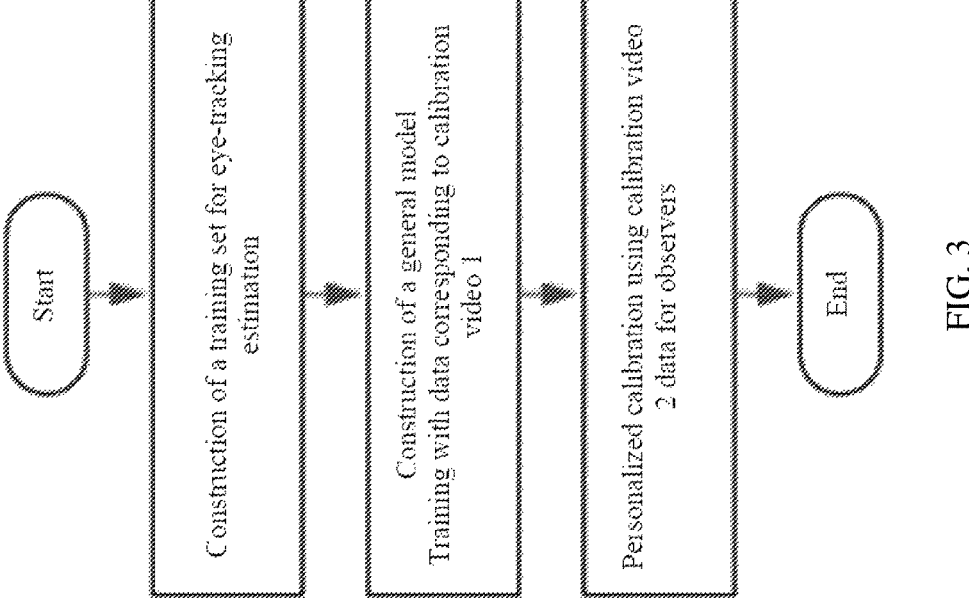
FIG. 3 is a flow chart of eye-tracking estimation in the present invention.

In order to obtain more accurate eye-tracking estimation results, according to FIG. 3, the general eye-tracking estimation model is first trained using the head-face video recorded by the smartphone camera during the playback of calibration video 1 in the data of m children with normal development, and then the general eye-tracking estimation results are individually calibrated using the head-face video recorded during the playback of calibration video 2. In the model training process, the center coordinates of the green origin of the corresponding video frames are used as the true values of eye-tracking estimation.

Figure 4:
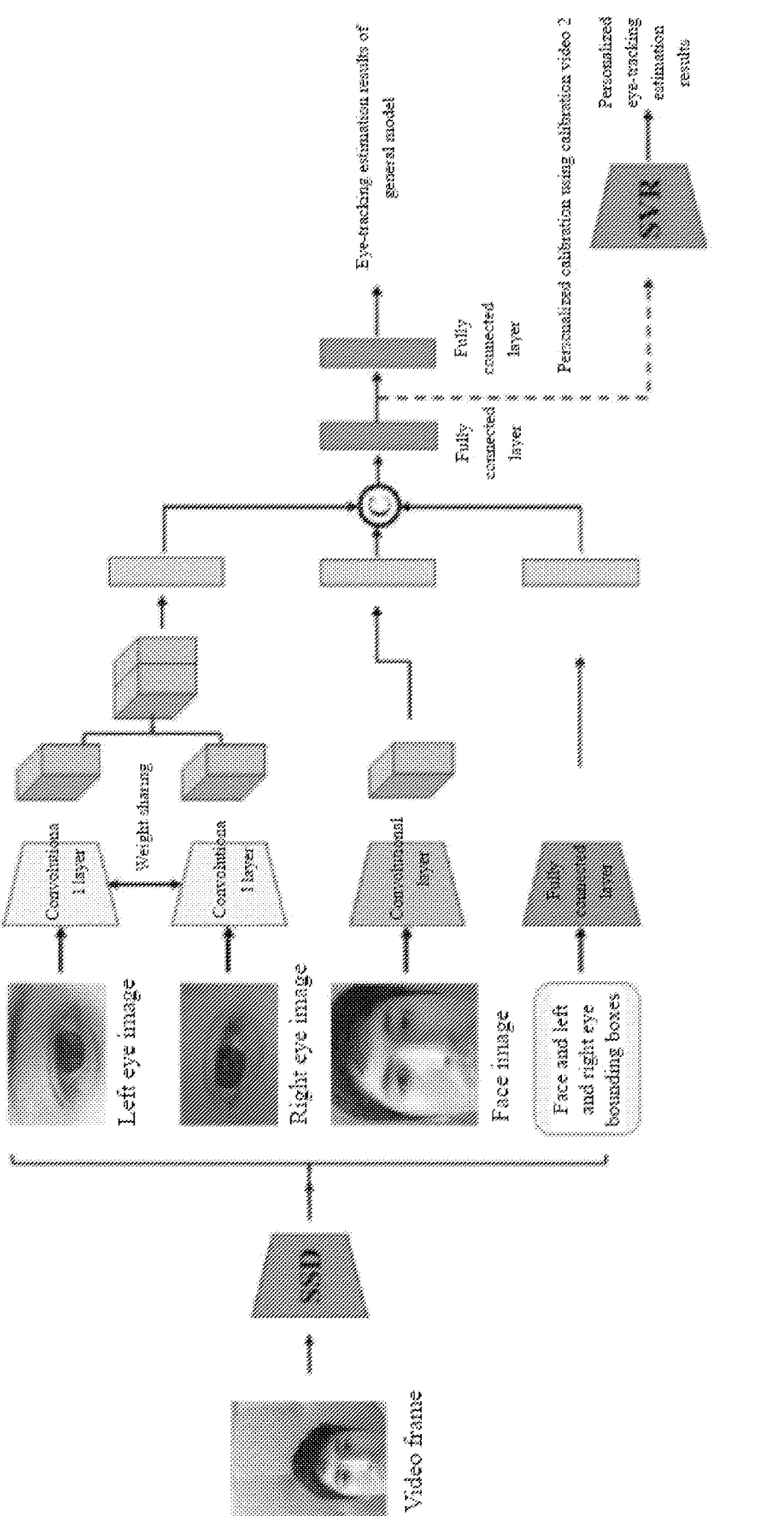
FIG. 4 is a diagram of the eye-tracking estimation network model in the present invention.

According to FIG. 4, first, the video frames are sampled from the head-face videos corresponding to the two calibration videos at 30 frames per second, and the face and left and right eyes in each frame are detected using a Single Shot MultiBox Detector (SSD) to obtain the face image, the left and right eye images, and the corresponding bounding boxes. Next, the face and left and right eye images are transformed into fixed size, the corresponding bounding boxes are normalized, and the features are extracted from the face and left and right eye images respectively by using the convolutional neural network, wherein the left and right eyes share the convolutional neural network weights. Then, the features of the corresponding bounding boxes are extracted by using the fully connected layer to obtain the relative location features of the face and left and right eyes in the images. Finally, the features extracted from the above-mentioned layers are fused by using the fully connected layer, and the final eye-tracking estimation results are obtained by the fully connected layer.

In the eye-tracking estimation model training, the general eye-tracking estimation model is first trained using the data of different observers corresponding to calibration video 1. However, since the general eye-tracking estimation model is trained from the data of different observers, and different observers have different intrinsic biases—the intrinsic optical axis visual axis bias (i.e., human kappa angle). Therefore, it is necessary to calibrate the general eye-tracking estimation model using the observer-specific data in calibration video 2 as the calibration training set to fit this inherent bias of different observers. This is done by using the fused features extracted from the general eye-tracking estimation model (i.e., the feature output of the penultimate layer of the general eye-tracking model) as input, and then using support vector regression (SVR) to obtain personalized calibration prediction results, and training the personalized SVR model with the data corresponding to the observer-specific calibration video 2, to obtain more accurate prediction results.

②Eye-Tracking Feature Extraction

Figure 5:
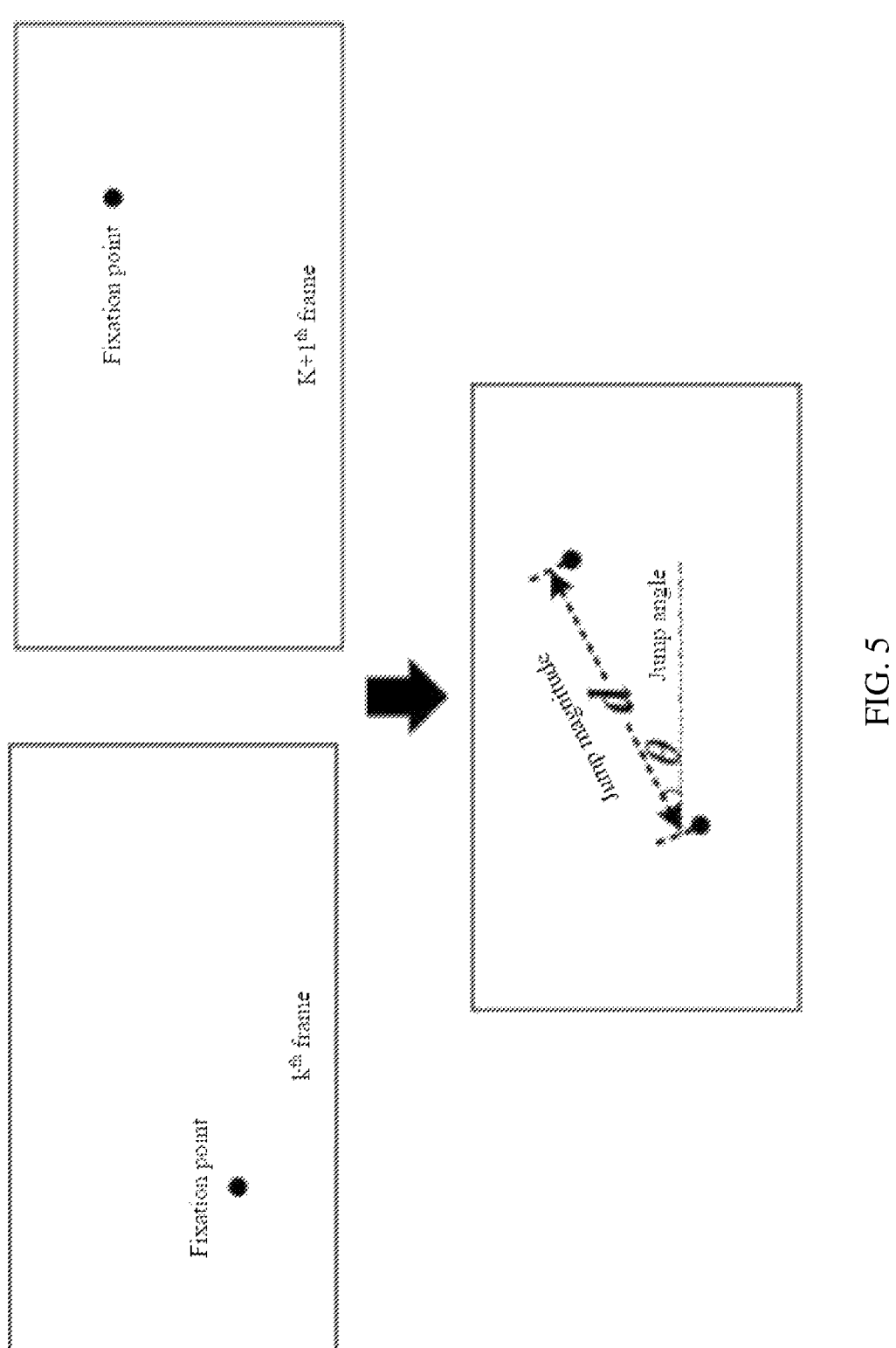
FIG. 5 is a schematic diagram of the fixation point jump amplitude and fixation point jump angle in the present invention.

The above eye-tracking estimation model is used to estimate the fixation point location of the head-face video frames corresponding to the testing video, and then the eye-tracking features are extracted from three perspectives, such as the fixation point jump amplitude, the fixation point jump angle and the number of fixation points in the semantic region. First, in order to extract the fixation point jump amplitude feature, according to FIG. 5, the Euclidean distance between the fixation point of every two adjacent frames in two-dimensional space is calculated and divided at 5 intervals. Second, in order to extract the fixation point jump angle feature, the angle between the jump line and the X-axis is calculated for the fixation point of every two adjacent frames, and then the 360 degrees is divided into 8 intervals uniformly and without jump to generate 9-dimensional histogram features.

Since the fixation point jump amplitude and the fixation point jump angle are the underlying eye-tracking features, in order to detect visual attention abnormalities from the perspective of semantic perception, first, the areas of interest of the video are marked, and three areas, including the face, the body, and other salient targets besides the human body are marked, and then the percentage of the number of fixation points of the face, body, other salient targets and background in each video to the total number of fixation points of the video is counted as semantic eye-tracking features. In summary, under the eye-tracking modality, each video will correspond to an 18-dimensional feature vector, wherein 14 dimensions are the histogram features of the underlying fixation point jump amplitude and fixation point jump angle, and 4 dimensions correspond to the percentage of fixation points in different semantic regions.

Step 3, Facial Expression Feature Extraction

First, the visual attention features of each head-face video under the testing video corresponding to the facial expression modality are extracted to prepare for training a multimodal visual attention abnormality screening model.

First, the face is detected using LibFaceDetection technology, and the face in the video is cropped. LibFaceDetection face detection is faster than the traditional MultiBox feedforward convolutional network algorithm and requires less computing power from the device. If no face is detected, the frame is classified as no face detected. If a face is detected, the segmented area is used for subsequent extraction and classification of facial expression features.

Figure 6:
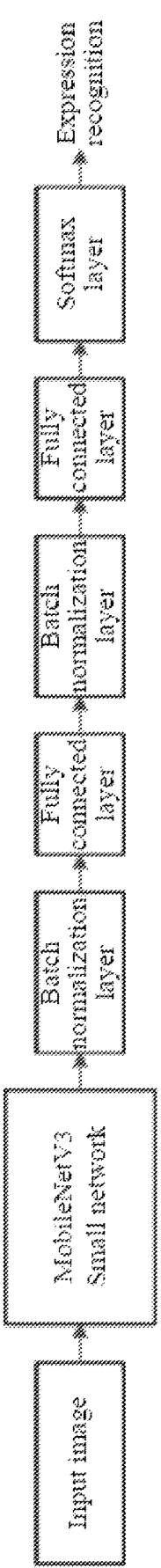
FIG. 6 is a diagram of the facial expression recognition network model in the present invention.

Next, according to FIG. 6, a MobileNetV3-Small network based on transfer learning is used to build a facial expression recognition network to achieve facial expression feature extraction from video data. The MobileNetV3-Small is a network model designed for mobile devices and embedded vision, which makes the model more lightweight and improves inference speed and model accuracy. Transfer learning is a machine learning method that allows a model trained for the first task to be used as an initial model for training a second, different task. In the specific training, ImageNet, an image recognition database is first used to train the MobileNetV3Small main network to obtain the initial parameters for network pre-training, and then two fully connected layers are added to the output of the Mobile-NetV3-Small network in turn, and a Batch Normalization (BN) layer is added before each fully connected layer. The final layer is connected to the Softmax layer to output the probabilities of seven facial expressions. Based on the construction of the complete facial expression recognition network, Extended Cohn-Kanade Dataset (CK+), a classical facial expression dataset is used to fine-tune the model globally to improve the recognition accuracy and obtain the facial expression recognition model based on the Mobile-NetV3-Small network.

Finally, the facial expression features are extracted and the histogram of facial expression features is constructed. Under each video frame, the face is detected and cropped using LibFaceDetection technology. If no face is detected, the video frame is marked as no face detected, and if a face is detected, the cropped face data is input to the trained facial expression recognition network for classification and recognition (7 categories of facial expressions: no expression, disgust, anger, sadness, fear, happiness, surprise). Finally, the facial expression recognition results of all frames in each video are counted to generate an 8-dimensional histogram of facial expressions (no expression, disgust, anger, sadness, fear, happiness, surprise, and no face detected). In summary, under the facial expression modality, each video corresponds to the features of the 8-dimensional histogram of facial expressions.

Step 4, Head Movement Feature Extraction

The visual attention features of each head-face video under the testing video corresponding to the head movement modality are extracted to prepare for training a multimodal model for screening visual attention abnormalities.

Head movement is also an important attribute in the visual attention process and can effectively respond to abnormal visual attention behavior. In the present invention, head movement features are described from two perspectives: head posture and head movement distance. In order to extract the head posture features, a constrained local neural field (CLNF) facial feature detector is first used to estimate different head posture angles, and then the head posture (down and up, turn left and turn right, skew to left and skew to right) is classified by setting thresholds. The head posture angles include head pitch angle p, head deviation angle y, and head roll angle r. According to the three head posture angles, the head postures are classified as follows:

$$\begin{cases} p_1(\text{Up}), \ p \leq -5° \\ p_2(\text{Still}), \ -5° \leq p \leq -5° \\ p_3(\text{Down}), \ p \geq 5° \end{cases}$$

$$\begin{cases} y_1(\text{Turn left}), \ y \leq -5° \\ y_2(\text{Still}), \ -5° \leq y \leq -5° \\ y_3(\text{Turn right}), \ y \geq 5° \end{cases}$$

$$\begin{cases} r_1(\text{Skew to left}), \ r \leq -5° \\ r_2(\text{Still}), \ -5° \leq r \leq -5° \\ r_3(\text{Skew to right}), \ r \geq 5° \end{cases}$$

In order to extract the head movement distance features, the 3D coordinates of the middle point of the two eyes are firstly estimated to locate the head, then the Euclidean distance of the head locating point on the stereoscopic space for every two adjacent frames is calculated to measure the head movement distance, and finally the head movement distance is divided quantitatively at five intervals. In conclusion, under the head movement modality, each video corresponds to a 14-dimensional histogram feature, wherein three head posture angles correspond to the division in 9-dimensional histogram of head posture, and the head movement distance corresponds to the division of 5 histogram intervals.

Step 5, the Construction of a Model for Screening Visual Attention Abnormalities Based on Multimodal Feature Fusion Based on the multimodal features such as the eye-tracking, the facial expressions and the head postures extracted from the above head-face video segments corresponding to the testing video, the task of this step is to construct multimodal feature sequences, and then use the LSTM network to establish the mapping relationship between the multimodal feature sequences and the classification labels.

Firstly, for the head-face videos of 50 children with autism and 50 children with normal development while watching the testing video, the head-face videos are sampled at a frequency of 10 frames per second, and finally M frames of data are extracted from the total video of each observer. Then the feature extraction is performed for one segment with 50 frames, and the multimodal feature sequence of each observer's video is $F=\{F_1, F_2, \ldots, F_i, \ldots\}$, where $F_i$ refers to the multimodal feature corresponding to 50 frames of data of the $i^{th}$ segment.

$F_i$ consists of the eye-tracking feature $ET_i$, the facial expression feature $FE_i$, and the head movement feature $HM_i$, i.e., $F_i=\{ET_i, FE_i, HM_i\}$, wherein $ET_i$ is the percentage feature of the 5-dimensional histogram of fixation point jump magnitude, 9-dimensional histogram of fixation point jump angle and 4-dimensional semantic region of fixation point (face, body, other significant targets and background) corresponding to the $i^{th}$ video segment; $ET_i$ corresponds to the 8-dimensional histogram of facial expressions, and $HM_i$ corresponds to the 9-dimensional histogram of head postures and the 5-dimensional histogram of head movement distances. In conclusion, each video segment corresponds to a 40-dimensional multimodal feature vector.

Finally, in order to train the model for screening visual attention abnormalities, the multimodal feature sequences extracted from the total video (multiple consecutive video segments) are used as input, and the corresponding labels (1 for children with autism and 0 for normal children) are used as an output to train the LSTM network and obtain the mapping relationship between the multimodal feature sequences and the labels to realize the construction of the model for screening visual attention abnormalities.

Step 6, the Recognition of Autism in Children to be Determined

For the children in the category to be determined, the head-face videos are first recorded while watching calibration video 2 and the testing video on smartphones, and the head-face videos corresponding to calibration video 2 are used to fine-tune the eye-tracking estimation network individually.

The head-face video corresponding to the testing video is sampled at a frequency of 10 frames per second, and then the video is segmented into a sequence of 50 frames. For each segment, the 40-dimensional features corresponding to the segment are generated by extracting the eye-tracking, facial expression, and head movement features corresponding to the segment, and then the features of the whole video corresponding to multiple segments are used to build a multimodal feature sequence, which is finally input to the LSTM network for autism recognition (1 for children with autism and 0 for normal children).

The present invention is different from a traditional visual attention differentiation research based on statistical analysis. The objective of the present invention is to construct a model for screening visual attention abnormalities, i.e., to collect the head-face videos of a child when watching the videos on the smartphone as model input, and directly determine whether the child's visual attention process is abnormal according to the trained model, rather than to simply compare the differences in the visual attention between different categories of people. In contrast to a traditional eye-tracker-based visual attention research, the present invention explores the eye-tracking estimation model based on mobile devices such as the smartphone to realize the screening of the visual attention abnormalities based on mobile devices, and reduce the cost of screening visual attention abnormalities to help solve difficult problem of screening children with diseases related to the visual attention abnormalities in remote areas. On the basis of the traditional visual attention research work based on eye-tracking alone, the present invention will extract the eye-tracking, the facial expressions, and the head posture features simultaneously, and use data from the same data source with different modalities for fusion recognition, so as to provide a more comprehensive analysis of children's visual attention process, reduce omission factors, and improve the abnormality recognition ability of the model.

The above content is only the description of embodiments of the present invention. However, the scope of protection for the present invention is not limited to this. Any person familiar with the technical field may easily think of various equivalent modifications or replacements within the technology scope disclosed in the present invention, and these modifications or replacements shall all fall within the protection scope of the present invention.

What is claimed is:

1. A method for screening mobile visual attention abnormalities in children based on multimodal data learning, comprising:

step 1: setting up at least a calibration video and a testing video, such that head-face videos of m children with visual attention abnormalities and m children with normal development while watching the calibration video and the testing video on smartphones are recorded, respectively, wherein m represents an integer having a value of two or greater;

step 2: constructing an eye-tracking estimation model, and subsequently estimating fixation point location from frames of the head-face videos corresponding to the testing video based on the eye-tracking estimation model, wherein eye-tracking features are extracted from fixation point jump magnitude, fixation point jump angle, and area of interest;

step 3: extracting facial expression features and head movement features from the head-face videos corresponding to the testing video and subsequently training a Long Short-Term Memory (LSTM) network to fuse different modal features to establish a mapping from multimodal features to category labels; and step 4: in a testing stage, head-face video of a child to be classified while watching videos on smartphones is recorded, such that the multimodal features including eye-tracking, facial expressions, and head movements are extracted and input into the trained LSTM network model to determine whether the child is abnormal.

2. The method of claim 1, wherein the step 1 includes:

playing calibration video 1, calibration video 2, and the testing video using a smartphone application, while the head-face videos corresponding to m children with abnormal visual attention and m children with normal development while watching the calibration video 1, the calibration video 2, and the testing video, are recorded, respectively, wherein:

the calibration video 1 is a 72-second video, with a black background, green dots, 40 dots flashing randomly, lit randomly for 1.8 seconds at each dot and varying in size by 18-50 pixels;

the calibration video 2 is a 72-second video, with a black background, green dots moving along the screen in a zigzag pattern, 1.8 seconds per dot, 40 dots moving smoothly;

the testing video is a 2-minute video, consisting of a short video of a children's puzzle game stitched together with a video of geometric changes; and the smartphone is placed horizontally with the children sitting at a distance of about 30 cm-40 cm from the smartphone to watch the videos, and the smartphone camera is used to record the head-face video while the videos are played.

3. The method of claim 1, wherein the constructing of the eye-tracking estimation model in step 2 includes:

sampling the frames from the head-face videos corresponding to two calibration videos, wherein face and left and right eyes in each frame are detected using a Single Shot MultiBox Detector to obtain a face image, left and right eye images, and corresponding bounding boxes;

transforming the face and left and right eye images into a fixed size, normalizing the corresponding bounding boxes, and exacting the features from the face and left and right eye images respectively by using a convolutional neural network, wherein the left and right eyes share the convolutional neural network weights;

extracting the corresponding bounding boxes by using a fully connected layer to obtain relative position features of the face and left and right eyes in the images; and fusing the features extracted from the above-mentioned layers by using a fully connected layer, wherein the final eye-tracking estimation results are obtained by the fully connected layer.

4. The method of claim 1, wherein the extracting of the facial expression features in step 3 includes:

in each of the frames, detecting and cropping a face using LibFaceDetection technology, wherein if no face is detected, the video frame is marked as no face detected, and if a face is detected, the cropped face data is input to a trained facial expression recognition network for classification and recognition; and generating a facial expression histogram based on facial expression recognition results from all frames in each video.

5. The method of claim 1, wherein in step 3 the head movement features include head posture features and head movement distance features, wherein extracting the head posture features includes:

using a constrained local neural domain facial feature detector to estimate different head posture angles, wherein the head postures are classified and divided by setting a threshold, wherein the head posture angles include: head pitch angle p, head deflection angle y and head roll angle r, and wherein according to three head posture angles, a specific division of head posture is shown as follows:

$$\begin{cases} p_1(\text{Up}), \ p \le -5° \\ p_2(\text{Still}), \ -5° \le p \le -5° \\ p_3(\text{Down}), \ p \ge 5° \end{cases}$$

$$\begin{cases} y_1(\text{Turn left}), \ y \le -5° \\ y_2(\text{Still}), \ -5° \le y \le -5° \\ y_3(\text{Turn right}), \ y \ge 5° \end{cases}$$

$$\begin{cases} r_1(\text{Skew to left}), \ r \le -5° \\ r_2(\text{Still}), \ -5° \le r \le -5° \ ; \\ r_3(\text{Skew to right}), \ r \ge 5° \end{cases}$$

and wherein extracting the head movement distance features includes:

estimating 3D coordinates of a middle point of two eyes to locate the head;

calculating a Euclidean distance of the head locating point on a stereoscopic space for every two adjacent frames to measure a head movement distance; and quantitatively dividing the head movement distance at five intervals.

6. The method of claim 5, wherein in step 3 the training of the LSTM network to establish the mapping from the multimodal feature sequences to the classification labels includes:

for the head-face videos of m children with visual attention abnormalities and m children with normal development while watching the testing video, sampling the head-face videos at a fixed frequency;

extracting M frames of data from the total video of each observer for feature extraction, wherein the multimodal feature sequence of each observer's video is denoted as $F=\{F_1, F_2, \ldots, F_i, \ldots\}$, in which:

$F_1$ refers to the multimodal feature corresponding to the $i^{th}$ paragraph;

$F_i$ consists of the eye-tracking feature $ET_i$, the facial expression feature $FE_i$, and the head movement feature $HM_i$, that is $F_i=\{ET_i, FE_i, HM_i\}$, in which $ET_i$ is the percentage feature of the 5-dimensional histogram of fixation point jump magnitude, 9-dimensional histogram of fixation point jump angle and 4-dimensional semantic region of fixation point corresponding to the $i^{th}$ video segment, $ET_i$ corresponds to the 8-dimensional histogram of facial expressions, and $HM_i$ corresponds to the 9-dimensional histogram of head postures and the 5-dimensional histogram of head movement distances;

training the LSTM network with the multimodal feature sequences extracted from multiple consecutive video segments as input and the corresponding labels as output, wherein the labels are marked as 1 for children with visual attention abnormalities and 0 for normal children; and obtaining the mapping relationship between multimodal feature sequences and labels to realize the construction of the model for screening visual attention abnormalities.

7. A computer system, comprising:

one or more processors;

a non-transitory computer readable storage medium for storing one or more programs, wherein the one or more programs, when executed by the one or more processors, enable the one or more processors to implement the method of claim 1.

8. A non-transitory computer readable storage medium, wherein the non-transitory computer readable storage medium stores computer executable instructions, and wherein the computer executable instructions, when executed, are operable to implement the method of claim 1.

* * * * *